United States Patent
Maschke

(10) Patent No.: US 7,013,511 B2
(45) Date of Patent: Mar. 21, 2006

(54) PATIENT BED

(75) Inventor: Michael Maschke, Lonnerstadt (DE)

(73) Assignee: Siemens Aktiengesellschaft, Munich (DE)

(*) Notice: Subject to any disclaimer, the term of this patent is extended or adjusted under 35 U.S.C. 154(b) by 31 days.

(21) Appl. No.: 10/939,317

(22) Filed: Sep. 10, 2004

(65) Prior Publication Data

US 2005/0055772 A1   Mar. 17, 2005

(30) Foreign Application Priority Data

Sep. 12, 2003 (DE) ................. 103 42 195

(51) Int. Cl.
*A61G 7/10* (2006.01)
*A61B 6/04* (2006.01)

(52) U.S. Cl. ........... 5/612; 5/88.1; 5/601; 378/209
(58) Field of Classification Search .......... 5/612, 5/83.1, 88.1, 601; 378/209
See application file for complete search history.

(56) References Cited

U.S. PATENT DOCUMENTS

| | | | |
|---|---|---|---|
| 3,302,219 A * | 2/1967 | Harris | 5/85.1 |
| 3,438,067 A * | 4/1969 | Saunders | 5/612 |
| 4,843,665 A * | 7/1989 | Cockel et al. | 5/88.1 |
| 5,018,225 A * | 5/1991 | Fergni et al. | 5/607 |
| 5,054,140 A * | 10/1991 | Bingham et al. | 5/600 |
| 5,138,646 A * | 8/1992 | Hubert et al. | 378/177 |
| 5,659,905 A * | 8/1997 | Palmer et al. | 5/88.1 |
| 6,295,666 B1 * | 10/2001 | Takaura | 5/88.1 |
| 6,651,281 B1 * | 11/2003 | Figiel | 5/612 |
| 2005/0055772 A1 * | 3/2005 | Maschke | 5/601 |

FOREIGN PATENT DOCUMENTS

| | | |
|---|---|---|
| DE | 196 27 657 C2 | 1/1998 |
| DE | 196 27 659 C1 | 1/1998 |
| GB | 2130482 A * | 6/1984 |
| GB | 2151472 A * | 7/1985 |
| WO | WO 97/20534 A1 | 6/1997 |

* cited by examiner

*Primary Examiner*—Robert G. Santos

(57) ABSTRACT

The invention relates to a patient bed having a frame (1) for supporting a mattress (3). To enable the insertion of an X-ray detector (9), it is proposed in accordance with the invention that a tensioning device (5a, 5b) is provided to secure a fabric-like carrier means (4) resting on a mattress (3) and a lifting device (6) is provided for lifting a patient (8) accommodated on the taut carrier means (4) from the mattress (3), so that an X-ray detector (9) can be inserted in a gap (10) formed between the lifted carrier means (4) and the mattress (3).

8 Claims, 2 Drawing Sheets

PATIENT BED

CROSS REFERENCE TO RELATED APPLICATIONS

This application claims priority to the German application No. 10342195.5, filed Sep. 12, 2003 and which is incorporated by reference herein in its entirety.

FIELD OF INVENTION

The invention relates to a patient bed having a frame, a mattress resting on a support fixed to the frame, and a tensioning device for tightening a cloth resting on the mattress.

BACKGROUND OF INVENTION

A patient bed of this kind is known for example from WO 97/20534 A1, said patient bed having a multi-element lifting device and swiveling device underneath the mattress which enables a bedridden patient to be transferred to and from the bed.

SUMMARY OF INVENTION

DE 196 27 657 C2 discloses an X-ray photograph device. The known X-ray photograph device is suitable for producing X-rays in the case of bedridden patients. In addition, a portable X-ray emitter is arranged above the patient. The patient is lifted by nursing staff and a flat detector accommodated in a cassette is then pushed under the patient. The lifting, in particular of heavy patients, can disadvantageously cause nursing staff to suffer back injuries.

A patient bed is proposed in DE 196 27 659 C1 which removes this disadvantage, whereby the flat detector is integrated into the mattress. The flat detector is connected to a mobile X-ray device by means of a cable. The manufacture of a patient bed of this kind is expensive due to the provision of the flat detector.

Therefore, an object of the invention is to eliminate the disadvantages of the prior art. In particular the invention is designed to specify a patient bed which is as simple and as cheap as possible to manufacture and allows X-ray photographs of bedridden patients to be produced more easily.

This object is achieved by the claims.

According to the invention, provision is made for a tensioning device to be secured to a fabric-like carrier means resting on the mattress and a lifting device for lifting a patient accommodated on the taut carrier means off the mattress, so that an X-day detector can be inserted into the gap formed between the lifted carrier means and the mattress. The proposed patient bed can be realized without any major technical outlay on the manufacturing side. The X-ray detector required for producing X-ray photographs is only inserted into the patient bed if an X-ray photograph is necessary. It is subsequently removed again and can be used for producing further X-ray photographs at other locations. As a result of the inventive provision of a lifting device and a tensioning device, it is no longer necessary, in order to insert the x-ray detector, to use nursing staff to lift the patient. Health problems suffered by the nursing staff as a result of lifting are avoided. Aside from this, the use of an inventive patient bed enables an X-ray photograph of a bedridden patient to be produced without the need for any nursing staff. Finally, the patient bed according to the invention allows a precise adjustment of the X-ray detector. Possible necessary multiple recordings as a result of inadequate adjustments are avoided. An X-ray detector can be a flat detector, for example a memory film, a solid-state matrix detector, a conventional X-ray film or the like which is accommodated in a cassette.

Advantageously the carrier means is preferably a reinforced woven sheet, a net or a plane. In particular the carrier means is configured such that it only stretches slightly when loaded with a normal patient weight. It is advantageously permeable to steam. Furthermore it is advantageous that the carrier means is manufactured from anti-allergenic material, for example woven Teflon.

The tensioning device can be fixed to a head side or foot side of the bed frame. The tensioning device is preferably fixed to the foot side of the frame, which facilitates the operation of the tensioning device. At the same time, the patient can be transferred to and from the bed in an unrestricted manner from both longitudinal sides of the patient bed. The tensioning device can include a shaft which is fixed to one side of the carrier means. The carrier means is tensioned simply by rotating the shaft. For these purposes one of the two opposite sides of the carrier means can be permanently fixed to the frame in a horizontal direction. The tensioning device can be operated manually, electrically or hydraulically.

According to a further embodiment the mattress rests on a support which is permanently fixed to the frame and the tensioning device can be moved using the lifting device in a vertical direction relative to the mattress. The proposed embodiment can be realized in a simple manner based on current patient beds. In particular, a support fixed to the frame for the mattress does not need to be modified for this embodiment.

According to an alternate embodiment the tensioning device is fixed permanently to the frame and the mattress can be moved using the lifting device in a vertical direction relative to the carrier means. Advantageously the lifting device can also be operated manually, electrically or hydraulically.

BRIEF DESCRIPTION OF THE DRAWINGS

An exemplary embodiment of the invention is illustrated below in more detail with reference to the drawings, in which.

DETAILED DESCRIPTION OF INVENTION

Figure 1:
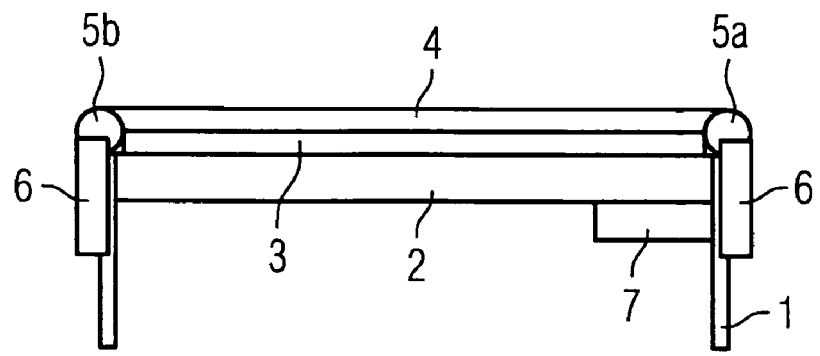
FIG. 1 shows a schematic side view of a patient bed

FIG. 1 shoes a schematic side view of a patient bed. A support 2 is fixed to a frame 1, on which a mattress 3 rests. A carrier means 4 rests on the mattress 3. A tensioning device for tensioning the carrier means 4 comprises a first shaft 5*a* fixed to the head end of frame 1, and a second shaft 5*b* fixed to a foot end of frame 1.

The carrier means 4 is advantageously manufactured from a tear resistant, barely stretchable woven fabric or similar. A fabric of this kind can be formed from plastic fibers for example. The fabric can be reinforced. The carrier means 4 is rectangular in shape. In this case, the narrow sides opposite each other are fixed to the first shaft 5a and second shaft 5b.

A lifting device is indicated by reference character 6, whereby the tensioning device can be moved in a vertical direction relative to the mattress 3. It is naturally also conceivable that the support 2 can be moved relative to the frame 1 by means of the lifting device 6. In this case, the tensioning device is permanently fixed to the frame 1. To actuate the tensioning device and/or lifting device 6, an electrically and/or hydraulically operated drive can be provided (not shown here). A control device is indicated using reference character 7 with which the electrically and/or hydraulically operated drive can be controlled.

In FIGS. 2 to 6, reference character 8 indicates a patient lying on the carrier means 3, reference character 9 indicates an X-ray detector accommodated in a cassette and reference character 10 indicates a gap between the carrier means 4 and the mattress 3.

The function of the patient bed is illustrated below with reference to FIGS. 2 to 6.

Figure 2:
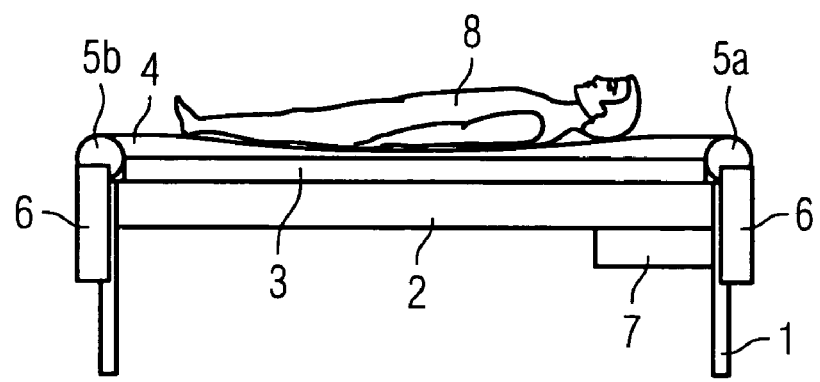
FIG. 2 shows the patient bed according to FIG. 1 with a patient accommodated thereon.

In FIG. 2 a patient 8 is lying on the carrier means 4. The carrier means 4 is not taut, said carrier means lying on the mattress 3 in a similar manner to a bed sheet.

Figure 3:
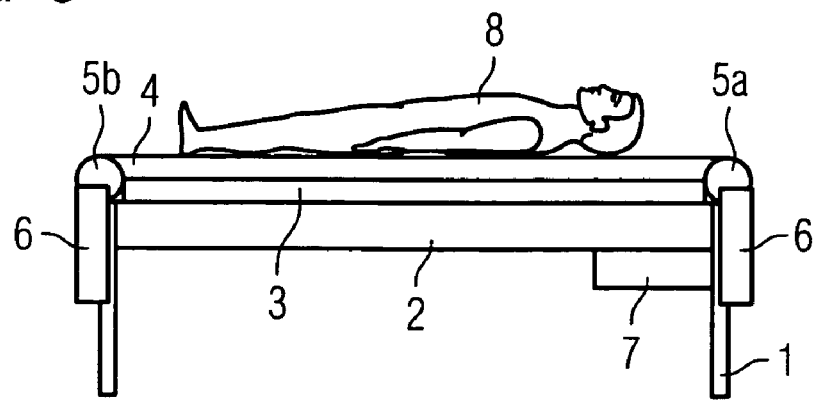
FIG. 3 shows the patient bed according to FIG. 2 with a taut carrier means.

To lift the patient 8, the carrier means is tensioned using an opposing rotation of the first shaft 5a and the second shaft 5b. The patient 4 is lifted slightly, as illustrated in FIG. 3.

Figure 4:
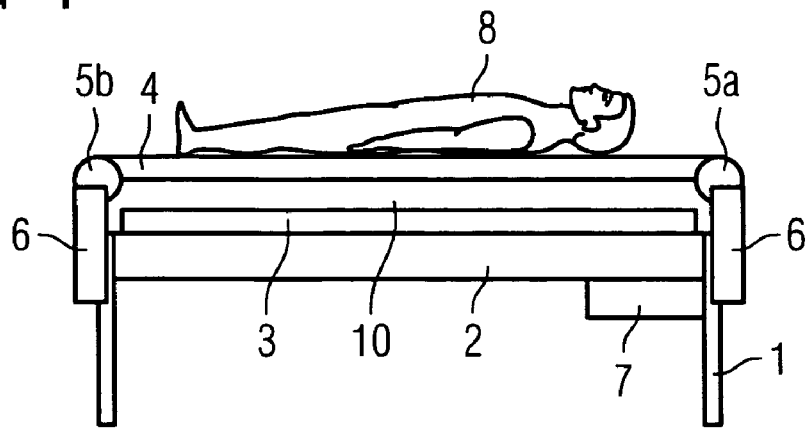
FIG. 4 shows the patient bed according to FIG. 3, whereby the carrier means and the patient are lifted from a mattress

Finally the tensioning device comprising the carrier means 4 and the shafts 5a, 5b, is lifted using the lifting device 6 from mattress 3, so that the recognizable gap 10 shown in FIG. 4 is formed between the carrier means 4 and the mattress 3.

Figure 5:
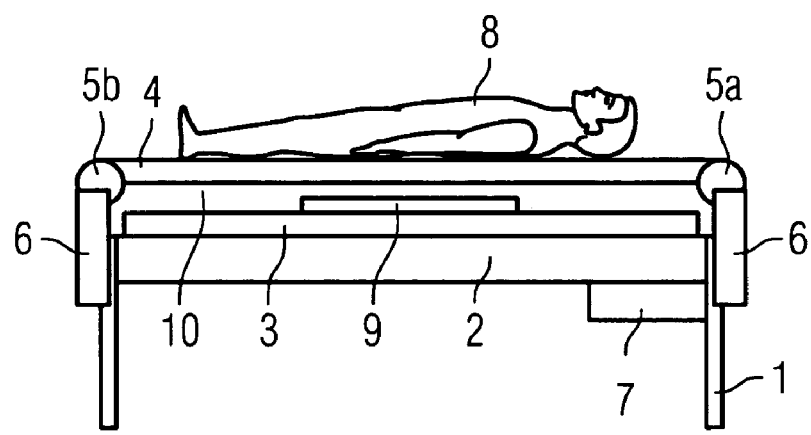
FIG. 5 shows the patient bed according to FIG. 4, with an inserted X-ray detector.
Figure 6:
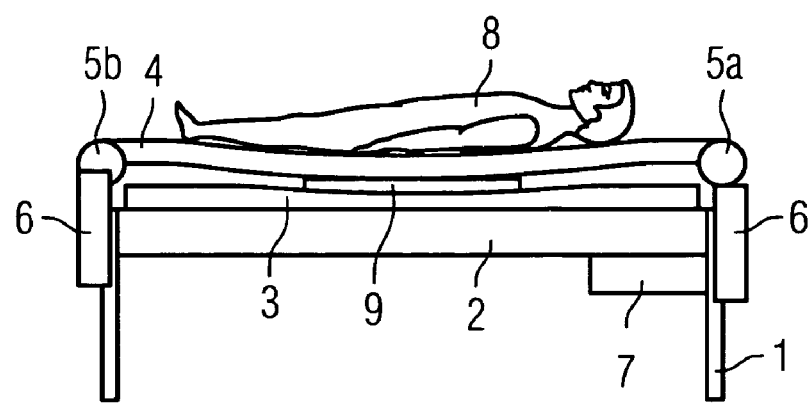
FIG. 6 shows the patient bed according to FIG. 5 whereby the carrier means is lowered onto the mattress and released

As illustrated in FIG. 5 an X-ray detector 9, for example a flat detector accommodated in a cassette, is then inserted into the gap 10. Subsequently the tensioning device 5a, 5b is lowered again by means of the lifting device 6, causing the carrier means 4 accommodating the patient to rest on the X-ray detector 9. The X-ray detector 9 is removed again after the X-ray photograph has been completed, and the above mentioned method steps are repeated.

The invention claimed is:

1. A patient bed, comprising:
   a frame;
   a mattress resting on a support fixed to the fame;
   a tensioning device for tightening a cloth resting on the mattress; and
   a lifting device for lifting a patient accommodated on the tightened cloth off the mattress, the lifting device adapted to move the tensioning device vertically, wherein the tensioning device comprises a shaft, a first end of the cloth is fixed to the shaft, and a second end opposite of the first end of the cloth is permanently fixed to the frame.

2. The patient bed according to claim 1, further comprising an X-ray detector inserted into a gap between the cloth and the mattress.

3. The patient bed according to claim 1, wherein the cloth is a fabric.

4. The patient bed according to claim 1, wherein the cloth is a tarpaulin.

5. The patient bed according to claim 1, wherein the tensioning device is fixed to a head end of the frame.

6. The patient bed according to claim 1, wherein the tensioning device is fixed to a foot end of the frame.

7. The patient bed according to claim 1, wherein the tensioning device is operated by a drive selected from the group consisting of manual, electrical and hydraulic.

8. The patient bed according to claim 1, wherein the lifting device is operated by a drive selected from the group consisting of manual, electrical and hydraulic.

* * * * *